United States Patent
Lawin et al.

(10) Patent No.: US 6,184,384 B1
(45) Date of Patent: Feb. 6, 2001

(54) DECHLORINATION OF PYRIDINES IN ACIDIC, ZINC-CONTAINING MEDIUMS

(75) Inventors: Phillip B. Lawin, New Brighton, MN (US); Z. Jason Yang, Florence, SC (US); L. Mark Huckstep, Danville, IN (US)

(73) Assignee: Reilly Industries, Inc., Indianapolis, IN (US)

( * ) Notice: Under 35 U.S.C. 154(b), the term of this patent shall be extended for 0 days.

(21) Appl. No.: 09/354,279

(22) Filed: Jul. 15, 1999

Related U.S. Application Data

(60) Provisional application No. 60/092,926, filed on Jul. 15, 1998.

(51) Int. Cl.$^7$ ................................................ C07D 213/61
(52) U.S. Cl. ........................................ 546/345; 546/346
(58) Field of Search ............................................... 546/345

(56) References Cited

U.S. PATENT DOCUMENTS

| | | | |
|---|---|---|---|
| 3,732,230 | 5/1973 | Brewer et al. | 546/345 |
| 3,993,654 | 11/1976 | Dean et al. | 546/345 |
| 4,111,938 | 9/1978 | Redemann | 546/180 |
| 4,127,575 | 11/1978 | McGregor | 546/345 |
| 4,258,194 | 3/1981 | Weis et al. | 546/345 |
| 4,259,495 | 3/1981 | Weis | 546/345 |
| 4,322,538 | 3/1982 | Vrieland et al. | 546/345 |
| 4,515,953 | 5/1985 | Marinak et al. | 546/345 |
| 4,659,835 | 4/1987 | Koranek | 546/345 |
| 4,703,123 | 10/1987 | Murphy | 546/345 |
| 5,591,857 | 1/1997 | Friis et al. | 546/296 |
| 6,051,714 * | 4/2000 | Lawin et al. | 546/345 |

FOREIGN PATENT DOCUMENTS

| | | | |
|---|---|---|---|
| 26 47 143 | 4/1978 | (DE) | C07D/213/61 |
| 1102261 | 2/1968 | (GB) | C07D/31/08 |
| 58-206564 | 5/1982 | (JP) | C07D/213/61 |
| 1121268 | 11/1987 | (JP) | C07D/213/61 |
| 03200769 | 12/1989 | (JP) | C07D/213/61 |
| 5-339235 | 6/1992 | (JP) | C07D/213/61 |
| 8-157457 | 11/1994 | (JP) | C07D/213/61 |

OTHER PUBLICATIONS

27266c, *Chemical Abstracts*, vol. 69 (1968).
59231t, *Chemical Abstracts*, vol. 116, p. 848 (1992).
T. Batkowski, D. Tomasik, P. Tomasik, "New Methods Of Pyridine Halogenation", *Ann. Soc. Chim. Polonorum*, vol. 41, pp. 2101–2104 (1967).
J. Bratt, B. Iddon, A.G. Mack, H. Suschitzky, J.A. Taylor, B.J. Wakefield, "Polyhalogenoaromatic Compounds. Part 41. Photochemical Dehalogenation and Arylation Reactions of Polyhalogenoaromatic and Polyhalogenoheteroaromatic Compounds", *J.C.S. Perkin I*, pp. 648–656 (1980).
W. Koenigs, R. Geigy, "Ueber einige Derivate des Pyridins. II.", 1884 CB 1832.
H. Meyer, R. Graf, "Üebr die Einwirkung von Thionylchlorid auf die Pyridin–monocarbonsäuren", *Jahrg.*, pp. 2202–221 (1928).
E. Plazek, A. Sorokowska, I.D. Tolopka, "Badania nad nitrowaniem chlorowcopochodnych pirydyny", *Roczniki Chemii*, vol. 18, pp. 210–216 (1938).
W.J. Sell, "The Chlorination of Methyl Derivatives of Pyridine. Part II. 2–Methylpyridine.", 1908 *JOC* 1993.
E.K. Shlenkova, N.S. Kupriyanova, O.L. Butkova, V. Ya. Katsobashvili, A.A. Beer, "Structure of the Products From Chlorination of β–Picoline" *J. Organic Chemistry of the USSR*, vol. 13, pp. 403–406 (1977).
P. Sutter, C.D. Weis, "The Specificity of Reductive Dechlorination in the Polychloropyridine Series. Synthesis of 2,3, 5–Trichloro–and of 2,3,5,6–Tetrachloropyridine", *J. Heterocyclic Chem.*, vol. 17, pp. 493–496 (May 1980).
J.P. Wibaut, J.R. Nicolai, "The Chlorination of Pyridine", *Recueil des Travaux Chimiques des Pays–Bas*, vol. 58, pp. 709–721 (1939).

\* cited by examiner

*Primary Examiner*—Alan L. Rotman
(74) *Attorney, Agent, or Firm*—Woodard, Emhardt, Naughton, Moriarty, & McNett

(57) ABSTRACT

Described are preferred processes for preparing 3,5-dichloropyridines by dechlorinating higher-chlorinated pyridine compounds such as 2,3,5,6-tetrachloropyridine in an acidic medium in the presence of zinc and optionally a quaternary ammonium catalyst.

22 Claims, No Drawings

US 6,184,384 B1

DECHLORINATION OF PYRIDINES IN ACIDIC, ZINC-CONTAINING MEDIUMS

REFERENCE TO RELATED APPLICATION

This application claims priority from U.S. patent application Ser. No. 60/092,926 filed Jul. 15, 1998, which is hereby incorporated herein by reference in its entirety.

BACKGROUND

The present invention resides generally in the field of chlorinated pyridines. More particularly, the present invention relates in one preferred aspect to processes for preparing 3,5-dichloropyridine by dechlorinating 2,3,5,6-tetrachloropyridine in an acidic medium such as that provided by an alkanoic acid, especially acetic acid.

As further background, polychlorinated pyridine derivatives are important intermediates in the preparation of pesticides. Consequently, much effort has been made at both the academic and industrial levels to find improved, economically-practicable processes for their preparation.

3,5-Dichloropyridine is one such intermediate. Proposed processes for its production have been widely diverse and have included both the selective chlorination of intermediate compounds, the selective dechlorination of higher-chlorinated pyridines, and other routes.

For example, JP011211268 (1989) describes the preparation of 3,5-dichloropyridine by dechlorinating chloropyridine compounds under catalytic hydrogenation conditions in the presence of palladium on carbon. JP 03200769 (1991) describes a process for oxidizing hydrazinopyridine derivatives to give chloropyridine compounds.

Despite work toward convenient and effective routes to 3,5-dichloropyridine, there remain needs for improved processes for the practicable, commercial-scale production this compound. The present invention is addressed to these needs.

SUMMARY OF THE INVENTION

A feature of the present invention is the discovery that 3,5-dichloropyridine can be selectively prepared by the dechlorination of higher-chlorinated pyridines in an acidic medium in the presence of zinc.

Accordingly, in one preferred embodiment, the invention provides a process for preparing 3,5-dichloropyridine which comprises dechlorinating a tri-, tetra- or pentachloropyridine compound having chlorines at the 3- and 5-positions, in an acidic medium including zinc, so as to selectively form 3,5-dichloropyridine. In a more preferred form, the invention provides for the preparation of 3,5-dichloropyridine by dechlorinating 2,3,5,6-tetrachloropyridine to selectively form 3,5-dichloropyridine in a medium including an alkanoic acid and zinc.

In a particularly preferred embodiment, the invention provides a process for selectively preparing 3,5-dichloropyridine by dechlorinating 2,3,5,6-tetrachloropyridine in acetic acid in-the presence of zinc.

Dechlorination processes as described herein can optionally be conducted in the presence of a quaternary ammonium catalyst, for example one having a cation of the formula:

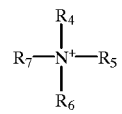

wherein:

$R_4$, $R_5$, and $R_6$, which may be the same as one another or may differ, are H; $C_1$ to $C_6$ alkyl, and wherein two of $R_4$, $R_5$ and $R_6$ may together as alkyl groups form a ring; $C_1$ to $C_6$ alkenyl; alkyl-phenyl, wherein the alkyl is $C_1$ to $C_6$ and the phenyl is optionally substituted with $C_1$ to $C_6$ alkyl, $C_1$ to $C_6$ alkenyl, halogen, hydroxyl, or $C_1$ to $C_6$ alkoxy; or phenyl, optionally substituted with $C_1$ to $C_6$ alkyl, $C_1$ to $C_6$ alkenyl, halogen, hydroxyl, or $C_1$ to $C_6$ alkoxy; and $R_7$ is $C_1$ to $C_6$ alkyl; $C_1$ to $C_6$ alkenyl; alkyl-phenyl, wherein the alkyl is $C_1$ to $C_6$ and the phenyl is optionally substituted with $C_1$ to $C_6$ alkyl, $C_1$ to $C_6$ alkenyl, halogen, hydroxyl, or $C_1$ to $C_6$ alkoxy; or phenyl, optionally substituted with $C_1$ to $C_6$ alkyl, $C_1$ to $C_6$ alkenyl, halogen, hydroxyl, or $C_1$ to $C_6$ alkoxy.

It has been found that the use of such catalysts speeds the reaction, while not eliminating the selectivity toward the desired 3,5-dichloropyridine product.

The present invention provides improved processes for preparing 3,5-dichloropyridines by the dechlorination of higher-chlorinated pyridine derivatives. The preferred processes are highly selective for the 3,5-dichloro- products, and can be conducted so as to achieve high conversion of the higher-chlorinated pyridine starting material. Additional preferred embodiments of the invention as well as their features and advantages will be apparent from the description that follows.

DESCRIPTION OF THE PREFERRED EMBODIMENTS

For the purposes of promoting an understanding of the principles of the invention, reference will now be made to certain of its embodiments and specific language will be used to describe the same. It will nevertheless be understood that no limitation of the scope of the invention is thereby intended, such alterations and modifications and applications of the principles of the invention as described herein being contemplated as would normally occur to one skilled in the art to which the invention pertains.

As disclosed above, the present invention features processes for preparing a 3,5-dichloropyridine compound by the dechlorination of a higher-chlorinated pyridine compound in an acidic medium in the presence of zinc. In particular aspects of the invention, provided are processes for selectively preparing 3,5-dichloropyridine by dechlorinating 2,3,5,6-tetrachloropyridine in a medium containing an alkanoic acid, especially acetic acid, and zinc.

In a general sense, the starting materials for processes of the invention will be encompassed by the formula:

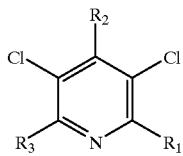

wherein $R_1$, $R_2$, and $R_3$, are H, chloro, or a non-interfering substituent such as a $C_1$ to $C_{20}$ hydrocarbon, e.g. alkyl, with the proviso that at least one of $R_1$, $R_2$, and $R_3$ is chloro. Illustrative starting materials thus include, for example, 2,3,4,5,6-pentachloropyridine, tetrachloropyridine compounds such as 2,3,5,6-tetrachloropyridine, optionally substituted at the 4-position with a non-interfering substituent as disclosed above, especially lower ($C_1$ to $C_6$) alkyl, and 2,3,4,5-tetrachloropyridine, optionally substituted at the 6-position with a non-interfering substituent as disclosed above, especially lower alkyl.

An especially preferred feature of the invention involves the discovery that 2,3,5,6-tetrachloropyridine can be selectively converted to 3,5-dichloropyridine in good yield by dechlorination in the presence of zinc in an acidic medium. The preferred starting material, 2,3,5,6-tetrachloropyridine

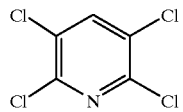

can be obtained commercially or can be prepared using procedures well known to the art and literature. For example, suitable processes by which 2,3,5,6-tetrachloropyridine can be made are disclosed in U.S. Pat. No. 5,591,857 issued Jan. 7, 1997 and the background literature discussed therein. As will be appreciated, this and other polychlorinated pyridine starting materials may be obtained from these or other known sources or chemical routes without departing from the present invention.

The selected chlorinated pyridine starting material is dechlorinated in the presence of zinc as an electron donor to form a 3,5-dichloropyridine compound. It is preferred that the zinc be used in particulate form to provide increased surface area for the reaction. Zinc chips or zinc dust may be used. As to amounts, it is preferred that at least 0.5 gram atoms of zinc be used per gram atom of chlorine to be removed. Typically, about 0.5 gram atoms to 3 gram atoms of zinc will be used per gram atom of chlorine to be removed, more preferably about 1 to 3 gram atoms of zinc per gram atom of chlorine. Thus, as an example, in the case of the dechlorination of 2,3,5,6-tetrachloropyridine to 3,5-trichloropyridine, it will be preferred to use about 1 to about 6 gram atoms of zinc per mole of 2,3,5,6-tetrachloropyridine. Most preferably in this case, about 2 to about 4 gram atoms of zinc are used per mole of 2,3,5,6-tetrachloropyridine.

As disclosed above, the inventive processes can optionally be conducted in the presence of a catalyst, such as a compound having both hydrophobic and hydrophilic character and traditionally used as a phase transfer catalyst. Preferred such compounds will demonstrate the capacity to increase the rate of reaction to form the desired dechlorinated pyridine derivative and assist in reducing the undesired agglomeration of the zinc particles. Preferred catalyst compounds include organic quaternary ammonium compounds. For example, the phase transfer catalyst can be provided by a cation encompassed by the formula:

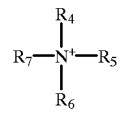

wherein:

$R_4$, $R_5$, and $R_6$, which may be the same as one another or may differ, are H; $C_1$ to $C_6$ alkyl, and wherein two of $R_4$, $R_5$ and $R_6$ may together as alkyl groups form a ring; $C_1$ to $C_6$ alkenyl; alkyl-phenyl, wherein the alkyl is $C_1$ to $C_6$ and the phenyl is optionally substituted with $C_1$ to $C_6$ alkyl, $C_1$ to $C_6$ alkenyl, halogen, hydroxyl, or $C_1$ to $C_6$ alkoxy; or phenyl, optionally substituted with $C_1$ to $C_6$ alkyl, $C_1$ to $C_6$ alkenyl, halogen, hydroxyl, or $C_1$ to $C_6$ alkoxy; and $R_7$ is $C_1$ to $C_6$ alkyl; $C_1$ to $C_6$ alkenyl; alkyl-phenyl, wherein the alkyl is $C_1$ to $C_6$ and the phenyl is optionally substituted with $C_1$ to $C_6$ alkyl, $C_1$ to $C_6$ alkenyl, halogen, hydroxyl, or $C_1$ to $C_6$ alkoxy; or phenyl, optionally substituted with $C_1$ to $C_6$ alkyl, $C_1$ to $C_6$ alkenyl, halogen, hydroxyl, or $C_1$ to $C_6$ alkoxy.

Within this formula, it is preferred that $R_4$, $R_5$, $R_6$, and $R_7$ all be organic (i.e. not H), and particularly preferred that they be alkyl, and most preferably $C_1$ to $C_4$ alkyl.

These preferred phase transfer catalyst compounds can be provided to the reaction mixture by a suitable salt, for example of the formula:

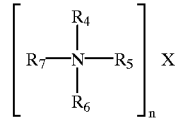

wherein $R_4$, $R_5$, $R_6$, and $R_7$ are as defined above, X is an anion having from 1 to 3 negative charges, and n is 1 to 3 and corresponds to the number of negative charges of X. Preferred anions, X, include halogens and hydroxy groups.

Other catalyst compounds may also be used, alone or in combination. For example, suitable catalysts include quaternary-forms of cyclic amines, e.g. N,N-dimethylpyrrolidinium salts, quaternary forms of diamines, e.g. diamine methyl quats such as ethylene diamine methyl quat, and the like. Still further compounds useful as catalysts in the invention include alcohols (including lower alkanols and longer-chain aliphatic alcohols), ethers (e.g. crown ethers), polyethers such as polyethylene glycol (PEG) of differing molecular weights, and other like compounds.

As to amounts, it is preferred that the catalyst compounds be charged generally in catalytic amount. As used in the art and herein, the term catalytic amount contemplates amounts which are less than stoichiometric relative to the relevant reactant (chlorinated pyridine compound). In the present invention, the catalyst, when included, will usually be used in the range of about 0.01 mole percent to 30 mole percent relative to the 2,3,5,6-tetrachloropyridine or other chlorinated pyridine starting material. Most preferably, the catalyst is charged in an amount of about 0.05 mole percent to about 10 mole percent relative to the polychlorinated pyridine starting material.

As disclosed above, processes of the invention are conducted in reaction medium containing an acid, and typically having a pH less than 8, more typically less than about 7.

The acidic medium is desirably provided by the inclusion of an organic acid such as a carboxylic acid. Alkanoic acids are preferred, including for example $C_1$ to $C_5$ alkanoic acids such as formic, acetic, propanoic, butanoic and pentanoic acids. Among these, acetic acid is preferred. Inorganic acids can also be used, for example HCl can be used in the presence of $NH_4Cl$.

Liquid organic acids can be used essentially neat as the reaction solvent, e.g. in the case of glacial acetic acid. Alternatively, the solvent system can include water and/or one or more organic solvents including, as examples, inert aliphatic solvents such as hexane, heptane, haloalkanes such as perchloroethylene or methylene chloride, and the like, and inert aromatic solvents such as benzene or alkyl benzene solvents including toluene, xylene, ethyl benzene, 2-chlorotoluene, as well as other benzene derivatives such as alkoxy benzenes, e.g. anisole. Preferred among these are aromatic solvents, more preferably toluene, mixed xylenes, or ortho-xylene.

Discussing now the procedures involved in the conduct of preferred inventive reactions, the reactants and solvent(s) can be charged all together prior to reacting, or one or more of the materials such as the zinc, catalyst, or acid can be all or partially dosed to the reaction mixture over the course of the reaction. For example, in one mode, processes of the invention are carried out while adding a portion of the zinc at the start of the procedure, and then periodically dosing the remainder of the zinc to the reaction mixture over the course of the reaction. This and similar variations will be apparent to the skilled artisan upon reviewing the disclosures herein.

As to temperature, preferred reactions of the invention are conducted at temperatures in the range of about 10° C. to about 150° C., including under reflux conditions. More preferably, these temperatures are in the range of about 20° C. to about 80° C. The reactions may be allowed to proceed adiabatically, and when so conducted the reaction exotherm will cause a rise in temperature over the course of the reaction. The reactions may also be conducted under isothermal conditions, with appropriate measures taken to remove heat generated by the exotherm. Relatedly, the reaction pressure utilized can generally be subatmospheric, atmospheric, or superatmospheric. As to duration, preferred inventive reactions will typically be complete in about 0.5 to about 24 hours, more preferably in the range of 1 to about 10 hours.

Reactions in accordance with the invention are preferably conducted with agitation of the reactor contents, for example by stirring. This assists in increasing the reaction rate and in preventing the undesired agglomeration of zinc particles.

As to results, preferred processes of the invention provide high yields and selectivity for 3,5-dichloropyridine, generally in excess of 60% isolated yields. In addition, chemical yields can readily be obtained in excess of 70% (based on GC analysis). Also advantageously, preferred processes of the invention provide high selectivity to 3,5-dichloropyridine. For example, 3,5-dichloropyridine can be produced in a selectivity above about 80% in more preferred processes.

Reacted mixtures of the invention can be worked up using general procedures known to the art. It is noted that upon completion of the reaction, there sometimes can occur a layer of agglomerated solids which can be filtered during workup. Layer separations, when needed, can be conducted in a conventional manner, with the 3,5-dichloropyridine product generally occurring in the organic layer. Such organic layers can be conventionally processed to obtain the chlorinated pyridine product in a purified form, for example by fractional distillation to achieve a purity of about 95% or greater.

The purified 3,5-dichloropyridine compounds produced in accordance with in the invention can be used in a conventional manner, and are known intermediates to pesticides and other useful compounds.

In order to provide a further understanding of the invention and its advantages, the following specific working Examples 1–8 are provided, and are summarized in Table 1, in which the following abbreviations are used: DCP=dichloropyridine; TCP=trichloropyridine; penta=pentachloropyridine; hr=hours; GC=gas chromatography. It will be understood that these examples are illustrative and not limiting of the invention.

EXAMPLE 1

A 1000 ml flask, equipped with a stirrer, reflux condenser, and thermometer, was charged with 2,3,5,6-tetrachloropyridine (Symtet) (54.2 grams, 0.25 mole), 250 ml of 95% acetic acid (5% water by weight), and tetramethylammonium bromide (0.51 grams, 0.0033 mole). The reaction mixture was warmed to 40° C. and zinc dust (49.04 grams, 0.75 mole) was added in 5 equal portions over a 2 hour period holding the reaction temperature to 40–50° C. The reaction mixture was then stirred for 6 hours at 40–50° C. The reaction mixture was diluted with water (250 ml) and the pH raised to 7.0 with 50% NaOH solution. The neutralized reaction mixture was extracted with toluene (100 ml) and the extract was analyzed by gas chromatography. Conversion of Symtet was 99.3% with a selectivity to 3,5-dichloropyridine (3,5-DCP) of 99%.

EXAMPLE 2

A 1000 ml flask, equipped with a stirrer, reflux condenser, and thermometer, was charged with Symtet (54.2 grams, 0.25 mole), 250 ml of glacial acetic acid, and tetramethylammonium bromide (0.55 grams, 0.0015 mole). With the reaction mixture at ambient temperature and stirring, zinc dust (35.18 grams, 0.538 mole) was added in 5 equal portions over a 2 hour period. An exothermic reaction slowly raised the reaction temperature to 75° C. where it was held for 5 hours then cooled to 60–65° C. and held for 17 hours. The reaction mixture was diluted with water (250 ml) and the pH raised to 6.9 with 50% NaOH solution. The neutralized reaction mixture was extracted with toluene (1×200 ml; 1×100 ml). The combined toluene extracts were analyzed by gas chromatography. Conversion of Symtet was 68.5% with a selectivity to 3,5-DCP of 97.2%.

EXAMPLE 3

A 1000 ml flask, equipped with a stirrer, reflux condenser, and thermometer, was charged with Symtet (54.2 grams, 0.25 mole) and 250 ml 95% acetic acid (5% water by weight). The reaction mixture was warmed to 40° C. and zinc dust (40.92 grams, 0.626 mole) was added in 4 equal portions over a 1.5 hour period holding the reaction temperature at 40–50° C. The reaction mixture was stirred for 17 hours at 40–50° C. It was noted, at the conclusion of this run, that some of the zinc had agglomerated and did not react. The reaction mixture was diluted with water (250 ml) and the pH raised to 7.0 with 50% NaOH solution. The neutralized reaction mixture was extracted with toluene (100 ml) and the toluene extract was analyzed by gas chromatography. Conversion of Symtet was 87.5% with a selectivity to 3,5-DCP of 98.3%.

EXAMPLE 4

A 1000 ml flask, equipped with a stirrer, reflux condenser, and thermometer, was charged with Symtet (54.2 grams, 0.25 mole), 250 ml of glacial acetic acid, sodium acetate (41.0 grams, 0.5 mole), and tetramethylammonium bromide (0.54 grams, 0.0035 mole). The reaction mixture was heated to 40° C. and zinc dust (37.0 grams, 0.566 mole) was added in 5 equal portions over a 2 hour period holding the temperature in the 40–50° C. range. The reaction mixture was then stirred at 40–50C. for 7 hours. The reaction mixture was diluted with water (250 ml) and the pH raised to 6.7 with 50% NaOH solution. The neutralized reaction mixture was extracted with toluene (2×100 ml) and the toluene extracts were combined for analysis. Conversion of Symtet was 72.5% with a selectivity to 3,5-DCP of 93.1%.

EXAMPLE 5

A 1000 ml flask, equipped with a stirrer, reflux condenser, and thermometer, was charged with Symtet (54.2 grams, 0.25 mole), 250 ml of 95% formic acid (5% water by weight), and tetramethylammonium bromide (0.53 grams, 0.0034 mole). The addition of zinc dust (35.19 grams, 0.538 mole) was started at ambient temperature and was added over a 2 hour period in 5 equal portions. The exothermic reaction raised the reaction temperature to 75°. The reaction mixture was stirred for 5 hours at adiabatic temperature then heated to 70–75° C. and held for 17 hours. The reaction mixture was diluted with water (250 ml) and the pH raised to 7.5 with 50% NaOH solution. The neutralized reaction mixture was extracted with toluene (1×200, ml; 1×100 ml) and the toluene extracts were combined for analysis by gas chromatography. Conversion of Symtet was 79.8% with a selectivity to 3,5-DCP of 93.4%.

EXAMPLE 6

A 500 ml flask, equipped with a stirrer, reflux condenser, and thermometer, was charged with Symtet (15.1 grams, 0.07 mole) and acetonitrile (199.0 grams). The reaction mixture was heated to reflux and zinc dust (9.15 grams, 0.14 mole) was added while stirring vigorously. A solution of ammonium chloride (15.11 grams, 0.282 mole) in water (40.2 grams) was added over a 45 minute period. The reaction mixture was then held, under reflux, for 3.5 hours. 12N Hydrochloric acid (18.1 grams) was slowly added to the reaction mixture and proceeded to distill overhead 164.8 grams of distillate at a head temperature of 77–78° C. The reaction mixture was diluted with 6.25N HCl (137.9 grams), heat removed, and stirred for one hour. The pH of the reaction mixture was raised to 7.0 with 50% NaOH solution (40 ml). The neutralized reaction mixture was extracted with toluene (100 ml) and the toluene extract was analyzed by gas chromatography. Conversion of Symtet was 49.2% with a selectivity to 3,5-DCP of 69.5%.

EXAMPLE 7

A 1000 ml flask, equipped with a stirrer, reflux condenser, and thermometer, was charged with pentachloropyridine (63.0 grams, 0.25 mole), 375 ml of 95% acetic acid (5% water by weight), and 25% tetramethylammonium hydroxide solution (1.37 grams, 0.0038 mole). The reaction mixture was heated to 50° C. and zinc dust (61.62 grams, 0.943 mole) was added in 4 equal portions over a 1.5 hour period holding the reaction temperature to a maximum of 50° C. The reaction mixture was then stirred overnight at 40–50° C. The reaction mixture was diluted with water (250 ml) and the pH raised to 7.0 with 50% NaOH solution. The neutralized reaction mixture was extracted with toluene (100 ml) and the toluene extract was analyzed by gas chromatography. Conversion of pentachloropyridine was 100% with a selectivity to 3,5-DCP of 92.1%.

EXAMPLE 8

A 100 ml flask, equipped with a stirrer, reflux condenser, and thermometer, was charged with Symtet (21.7 grams, 0.1 mole), glacial acetic acid (20 ml), benzene (50 ml), water (50 ml), and tetramethylammonium bromide (0.2 grams, 0.0013 mole). Zinc dust (14 grams, 0.21 mole) was added at room temperature and the reaction was allowed to proceed adiabatically reaching a maximum temperature of 45° C. The reaction was allowed to proceed for 7 hours. Analysis of the benzene layer was performed by gas chromatography. Conversion of Symtet was 50.6% with a selectivity to 3,5-DCP of 85.8%.

TABLE 1

| Example | Symtet (moles) | Solvent (ml) | Catalyst (moles) | Zinc (moles) | Temp (° C.) | Time (hr) | Conversion (GC %) | 3,5-DCP | 2,5-DCP | 2,3,5-TCP | 2,3,6-TCP | Symtet | Penta |
|---|---|---|---|---|---|---|---|---|---|---|---|---|---|
| 1 | 0.25 | 95% AcOH 250 | TMAB 0.0033 | 0.75 | 40–50 | 8 | 99.3 | 98.4% | 0.0% | 0.1% | 0.0% | 0.7% | — |
| 2 | 0.25 | 100% AcOH 250 | TMAB 0.0015 | 0.538 | 60–75 | 24 | 68.5 | 66.6% | 0.0% | 1.6% | 0.0% | 31.5% | — |
| 3 | 0.25 | 95% AcOH 250 | None | 0.626 | 40–50 | 18.5 | 87.5% | 86.0% | 0.0% | 1.2% | 0.0% | 12.5% | — |
| 4 | 0.25 | 100% AcOH 250 NaOAc 0.5 mole | TMAB 0.0035 | 0.566 | 40–50 | 9 | 72.5% | 67.5% | 0.0% | 4.1% | 0.2% | 27.5% | — |
| 5 | 0.25 | 95% Formic 250 | TMAB 0.0034 | 0.538 | 70–75 | 24 | 79.8% | 74.5% | 0.0% | 2.6% | 0.0% | 20.2% | — |
| 6 | 0.07 | CH3CN 250 NH4Cl 0.282 mole HCl 0.9 mole | None | 0.14 | 77–78 | 4.25 | 49.2% | 34.2% | 0.0% | 3.7% | 1.5% | 50.8% | — |
| 7 | Penta 0.25 | 95% AcOH 375 | TMAH 0.0038 | 0.943 | 40–50 | 18.5 | 100% | 92.1% | 0.0% | 0.8% | 0.0% | 7.1% | 0.0% |

TABLE 1-continued

| Example | Symtet (moles) | Solvent (ml) | Catalyst (moles) | Zinc (moles) | Temp (° C.) | Time (hr) | Conversion (GC %) | 3,5-DCP | 2,5-DCP | 2,3,5-TCP | 2,3,6-TCP | Symtet | Penta |
|---|---|---|---|---|---|---|---|---|---|---|---|---|---|
| 8 | 0.1 | 100% AcOH 20 Benzene 50 Water 50 | TMAB 0.0013 | 0.2 | 25–45 | 7 | 50.6% | 43.4% | 0.0% | 6.3% | 0.0% | 49.4% | — |

While the invention has been described in detail above with reference to specific embodiments, it will be understood that modifications and alterations in the embodiments disclosed may be made by those practiced in the art without departing from the spirit and scope of the invention. All such modifications and alterations are intended to be covered. In addition, all publications cited herein are indicative of the level of skill in the art and are hereby incorporated by reference in their entirety as if each had been individually incorporated by reference and fully set forth.

What is claimed is:

1. A process for preparing 3,5-dichloropyridine, comprising:
   dechlorinating a tri-, tetra- or pentachloropyridine compound including chlorines at the 3- and 5-positions of the pyridine ring in an acidic reaction medium including zinc to selectively form a 3,5-dichloropyridine compound.

2. The process of claim 1, wherein the reaction medium includes an alkanoic acid.

3. The process of claim 1, wherein the alkanoic acid is a $C_1$ to $C_5$ alkanoic acid.

4. The process of claim 3, wherein the alkanoic acid is acetic acid.

5. The process of claim 1, wherein the reaction medium also includes a catalyst having a cation of the formula:

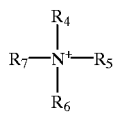

wherein:
   $R_4$, $R_5$, and $R_6$, which may be the same as one another or may differ, are H; $C_1$ to $C_6$ alkyl, and wherein two of $R_4$, $R_5$ and $R_6$ may together as alkyl groups form a ring; $C_1$ to $C_6$ alkenyl; alkyl-phenyl, wherein the alkyl is $C_1$ to $C_6$ and the phenyl is optionally substituted with $C_1$ to $C_6$ alkyl, $C_1$ to $C_6$ alkenyl, halogen, hydroxyl, or $C_1$ to $C_6$ alkoxy; or phenyl, optionally substituted with $C_1$ to $C_6$ alkyl, $C_1$ to $C_6$ alkenyl, halogen, hydroxyl, or $C_1$ to $C_6$ alkoxy; and
   $R_7$ is $C_1$ to $C_6$ alkyl; $C_1$ to $C_6$ alkenyl; alkyl-phenyl, wherein the alkyl is $C_1$ to $C_6$ and the phenyl is optionally substituted with $C_1$ to $C_6$ alkyl, $C_1$ to $C_6$ alkenyl, halogen, hydroxyl, or $C_1$ to $C_6$ alkoxy; or phenyl, optionally substituted with $C_1$ to $C_6$ alkyl, $C_1$ to $C_6$ alkenyl, halogen, hydroxyl, or $C_1$ to $C_6$ alkoxy.

6. The process of claim 5, wherein the reaction medium includes a $C_1$ to $C_5$ alkanoic acid.

7. The process of claim 6, wherein the alkanoic acid is acetic acid.

8. The process of claim 1, wherein the reaction medium is homogeneous.

9. The process of claim 1, wherein the reaction medium is heterogeneous.

10. The process of claim 1, which comprises dechlorinating 2,3,5,6,-tetrachloropyridine to selectively form 3,5-dichloropyridine.

11. A process for producing 3,5-dichloropyridine, comprising dechlorinating a pyridine compound of the formula:

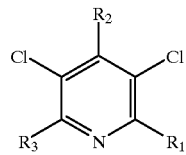

wherein $R_1$, $R_2$, and $R_3$, are H, chloro, or a $C_1$ to $C_{20}$ hydrocarbon group, with the proviso that at least one of $R_1$, $R_2$, and $R_3$ is chloro, in the presence of zinc in an acidic reaction medium, to form a corresponding 3,5-dichloropyridine compound.

12. The process of claim 11, wherein said acidic reaction medium includes an organic acid.

13. The process of claim 12, wherein said organic acid is a carboxylic acid.

14. The process of claim 13, wherein said carboxylic acid is an alkanoic acid.

15. The process of claim 14, wherein said alkanoic acid is formic or acetic acid.

16. The process of claim 11, wherein said reaction medium also includes a quaternary ammonium catalyst.

17. The process of claim 15, wherein said quaternary ammonium catalyst has a cation of the formula:

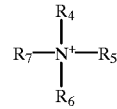

wherein:
   $R_4$, $R_5$, and $R_6$, which may be the same as one another or may differ, are H; $C_1$ to $C_6$ alkyl, and wherein two of $R_4$, $R_5$ and $R_6$ may together as alkyl groups form a ring; $C_1$ to $C_6$ alkenyl; alkyl-phenyl, wherein the alkyl is $C_1$ to $C_6$ and the phenyl is optionally substituted with $C_1$ to $C_6$ alkyl, $C_1$ to $C_6$ alkenyl, halogen, hydroxyl, or $C_1$ to $C_6$ alkoxy; or phenyl, optionally substituted with $C_1$ to $C_6$ alkyl, $C_1$ to $C_6$ alkenyl, halogen, hydroxyl, or $C_1$ to $C_6$ alkoxy; and
   $R_7$ is $C_1$ to $C_6$ alkyl; $C_1$ to $C_6$ alkenyl; alkyl-phenyl, wherein the alkyl is $C_1$ to $C_6$ and the phenyl is optionally substituted with $C_1$ to $C_6$ alkyl, $C_1$ to $C_6$ alkenyl, halogen, hydroxyl, or $C_1$ to $C_6$ alkoxy; or phenyl, optionally substituted with $C_1$ to $C_6$ alkyl, $C_1$ to $C_6$ alkenyl, halogen, hydroxyl, or $C_1$ to $C_6$ alkoxy.

18. The process of claim 17, wherein said reaction medium includes acetic acid.

19. A process for selectively preparing 3,5-dichloropyridine, comprising dechlorinating 2,3,5,6,-tetrachloropyridine in acetic acid in the presence of zinc to selectively form 3,5-dichloropyridine.

20. The process of claim 19, wherein said dechlorinating is performed in the presence of a quaternary ammonium catalyst.

21. The process of claim 11, wherein said acidic medium includes an aqueous carboxylic acid.

22. The process of claim 11, wherein said acidic medium includes HCl and $NH_4Cl$.

* * * * *

UNITED STATES PATENT AND TRADEMARK OFFICE
CERTIFICATE OF CORRECTION

PATENT NO.     : 6,184,384 B1
DATED          : February 6, 2001
INVENTOR(S)    : Lawin et al.

It is certified that error appears in the above-identified patent and that said Letters Patent is hereby corrected as shown below:

Title page,
Item [56], References Cited, OTHER PUBLICATIONS, please change "2202-221 (1928)" to -- 2202-2215 (1928) --.
OTHER PUBLICATIONS, please change "β-Picoline" to -- α-Picoline --.

Columns 9 and 10,
In TABLE 1-continued, line 11, please align the numeral "50" under the word "Water" under heading SOLVENT (ml).

Signed and Sealed this

Twenty-seventh Day of August, 2002

Attest:

Attesting Officer

JAMES E. ROGAN
Director of the United States Patent and Trademark Office